United States Patent
Croizat et al.

(10) Patent No.: US 9,452,247 B2
(45) Date of Patent: Sep. 27, 2016

(54) DEVICE FOR NEGATIVE PRESSURE WOUND THERAPY

(75) Inventors: Pierre Croizat, Herbrechtingen (DE); Axel Eckstein, Heidenheim (DE); Ulrich Fink, Heidenheim (DE)

(73) Assignee: Paul Hartmann AG, Heidenheim (DE)

( * ) Notice: Subject to any disclaimer, the term of this patent is extended or adjusted under 35 U.S.C. 154(b) by 994 days.

(21) Appl. No.: 12/970,125

(22) Filed: Dec. 16, 2010

(65) Prior Publication Data

US 2011/0144599 A1 Jun. 16, 2011

Related U.S. Application Data

(60) Provisional application No. 61/286,842, filed on Dec. 16, 2009.

(51) Int. Cl.
| | | |
|---|---|---|
| *A61M 5/00* | (2006.01) | |
| *A61M 1/00* | (2006.01) | |
| *A61M 27/00* | (2006.01) | |
| *A61F 13/02* | (2006.01) | |
| *A61M 5/32* | (2006.01) | |
| *A61M 25/00* | (2006.01) | |
| *A61M 35/00* | (2006.01) | |
| *A61M 5/178* | (2006.01) | |
| *A61F 13/00* | (2006.01) | |

(52) U.S. Cl.
CPC ...... *A61M 1/0088* (2013.01); *A61F 13/00068* (2013.01); *A61F 13/0216* (2013.01); *A61F 13/0223* (2013.01); *A61F 13/0226* (2013.01); *A61M 27/00* (2013.01); *A61F 2013/00536* (2013.01)

(58) Field of Classification Search
CPC ........ A61M 5/00; A61M 5/32; A61M 25/00; A61M 35/00; A61M 1/00; A61M 5/178; A61F 13/00; A61F 7/00
USPC ................ 604/311, 312, 313, 315, 316, 318
See application file for complete search history.

(56) References Cited

U.S. PATENT DOCUMENTS

| | | | |
|---|---|---|---|
| 5,584,801 A * | 12/1996 | Kuroyanagi et al. | ........... 602/47 |
| 5,636,643 A | 6/1997 | Argenta et al. | |
| 5,645,081 A | 7/1997 | Argenta et al. | |
| 8,410,239 B2 * | 4/2013 | Blanc et al. | .................... 528/32 |

(Continued)

FOREIGN PATENT DOCUMENTS

| | | |
|---|---|---|
| EP | 0 691 113 A1 | 1/1996 |
| GB | 2 185 747 A | 7/1987 |

(Continued)

*Primary Examiner* — Tatyana Zalukaeva
*Assistant Examiner* — Ilya Treyger
(74) *Attorney, Agent, or Firm* — Jason D. Voight (57) ABSTRACT

The invention refers to a device for the negative pressure wound therapy comprising a cover material for the air-tight sealing of the wound and the wound surroundings; a means suitable for the generation of a negative pressure in the wound area, preferably a means for the functional connection of the wound area with a negative pressure source outside of the cover material in such a way that a negative pressure can be generated in the wound area and fluids can be drawn out of the wound area by suction; and a wound dressing, whereby the wound dressing contains an open-cell foam on the basis of a cross-linked polyorganosiloxane. The invention also refers to the use of open-cell foam on the basis of a cross-linked polyorganosiloxane for use in the negative pressure wound therapy, in particular in patients with a BMI of less than 18.

20 Claims, 2 Drawing Sheets

(56) References Cited

U.S. PATENT DOCUMENTS

| | | |
|---|---|---|
| 2007/0185426 A1 | 8/2007 | Ambrosio et al. |
| 2007/0225663 A1 | 9/2007 | Watt et al. |
| 2008/0004559 A1 | 1/2008 | Riesinger |
| 2008/0009812 A1 | 1/2008 | Riesinger |
| 2009/0227969 A1 | 9/2009 | Jaeb et al. |
| 2010/0003484 A1 | 1/2010 | Blanc et al. |

FOREIGN PATENT DOCUMENTS

| | | |
|---|---|---|
| GB | 2 415 908 A | 1/2006 |
| RU | 22749 U1 | 4/2002 |
| WO | 01/89431 A1 | 11/2001 |
| WO | 2005/123170 A1 | 12/2005 |
| WO | 2006/052839 A2 | 5/2006 |
| WO | 2007/141250 A1 | 12/2007 |

* cited by examiner

DEVICE FOR NEGATIVE PRESSURE WOUND THERAPY

This application claims the benefit of U.S. Provisional Application No. 61/286,842, filed Dec. 16, 2009.

The invention relates to a device for negative pressure wound therapy comprised of a cover material for air-tight sealing of the wound and the surrounding area, a means for the generation of a negative pressure in the wound area, in particular for the functional connection of the wound area with a negative pressure source outside of the cover material so that a negative pressure can be generated in the wound area and fluids can be drawn out of the wound area by suction; and an open-cell foam on the basis of a cross-linked polyorganosiloxane as a wound dressing. The invention further relates to the use of an open-cell foam on the basis of a cross-linked polyorganosiloxane for use in negative pressure wound therapy.

A wound is defined as the separation of the coherence of tissues of the outer body of humans or animals. It can result in a loss of substance.

Devices for the negative pressure wound therapy are known in the state of the art.

For example WO 1993/009727 A1 describes a device to promote healing of the wound by the application of a negative pressure on the skin area which is wounded and the area around the wound. The device subject to WO 1993/009727 A1 includes a negative pressure device to generate the negative pressure, an air-tight cover of the wound which has a functional connection to the negative pressure device, as well as a dressing for positioning on the wound inside the air-tight cover. The dressing is preferably of an open-cell polymer foam, for example polyester foam.

Alongside the use of open-cell polymer foam, other materials suitable for dressings in negative pressure wound therapy were also described.

WO 2001/89431 A1 describes a collagen matrix as a dressing for the negative pressure wound therapy.

GB 2 415 908 describes the use of fibrous material which can also be bio-resorbable in dressings for the negative pressure wound therapy.

WO 2006/52839 A1 describes the use of dry, fibrous material or a fibrous mixture as a wound contact layer for the negative pressure wound therapy. During the negative pressure wound therapy, the fibrous material soaks up wound exudate to form a gel.

WO 2005/123170 A1 discloses dressings for the negative pressure wound therapy, with which undesirable substances are inactivated or removed from the wound area and/or desirable substances present in the wound area are concentrated. As suitable constituents for the intended purpose, WO 2005/123170 proposes a wide range of initially dry polymers which can form a gel by taking water from the wound exudate.

WO 2006/048246 A1 describes a multi-component dressing for the negative pressure wound therapy which has a super-absorbent polymer. The super-absorbent polymer can be enclosed by a fluid-permeable shell and form a dry absorption body over the wound area.

Devices for the negative pressure wound therapy are commercially available, for example the V.A.C.® device from the company KCl. Commercially available devices often use a dressing which contains an open-cell polymer foam such as polyvinyl alcohol (PVA) or polyurethane (PU).

The commercially available foam dressings are compressed to a different degree, depending on the negative pressure applied. This can cause a constriction of the passages necessary for the removal of the wound exudate. In addition to this, prolonged use of polyvinyl alcohol or polyurethane foam in the negative pressure wound therapy can lead to the adhesion of the foam to the wound. When the dressing is to be changed, additional measures have to be taken to remove adhered foam, for example by rinsing with Ringer's solution. Tissue which has grown into the foam can lead to a tissue traumatization when the dressing is removed and thus delay the healing process.

It has also been shown that the usual polymer foams of polyvinyl alcohol (PVA) or polyurethane (PU) are only suitable to a limited extent for longer dressing-change intervals. First, it has been established that there is an undesirable flow rate reduction within 3 days. Patients also often find the usual dressings unpleasant when they are on the wound for longer than 3 days without being changed. When the dressing is changed after 3 days or more, there are often unpleasant odors. The germ density is undesirably high.

It has also been shown that the usual polymer foams of polyvinyl alcohol (PVA) or polyurethane (PU) can also get stuck to the cover material.

Furthermore, it has also been shown, particularly in the use of PVA foams, that the suction power is undesirably reduced depending on the port. Also, PVA is only elastic in a moist condition which means that preconditioning is essential.

It is the object of the present invention to further improve the negative pressure wound therapy and to overcome the disadvantages of the current state of the art. The invention provides devices and methods for the negative pressure wound therapy, with which a therapy can be carried out as effectively as possible and as comfortably as possible for the patient.

In particular, the present invention should allow a negative pressure wound therapy which enables the patient to change the dressing at intervals of 3 days or more. During the interval the dressing should be subjectively perceived by the patient as pleasant. There should be no itching or reddening of the skin. When the dressing is changed after a period of 3 days, there should be as little unpleasant odor as possible. The germ density in the exchanged dressing should be low. Even at longer dressing-change intervals, the formation of physiologically undesirable substances should be avoided.

The object is to provide a wound dressing which avoids, as far as possible, adhesion with the cover material. The suction power should not be reduced in dependence of the port.

Unexpectedly, the objects could be solved by the use of a dressing which contains an open-cell foam on the basis of a cross-linked polyorganosiloxane. Surprisingly, it was found that a device for negative pressure wound therapy including at least a dressing, whereby the dressing contains an open-cell foam on the basis of a cross-linked polyorganosiloxane, is especially suitable for an advantageous, i.e. very effective, treatment of wounds which is very comfortable for the patient.

The invention thus solves the object with a device for the negative pressure wound therapy with the features described herein, and with an open-cell foam on the basis of a cross-linked polyorganosiloxane for use in the negative pressure wound therapy as described herein.

The object of the invention is thus a device for the negative pressure wound therapy, comprising
(a) a cover material for air-tight sealing of the wound and the surrounding area,
(b) a means for the generation of a negative pressure in the wound area, preferably a means for the functional connection of the wound area with a negative pressure source outside of the cover material so that a negative pressure can be generated in the wound area and fluids can be drawn out of the wound area by suction,
(c) an open-cell foam on the basis of a cross-linked polyorganosiloxane as a wound dressing.

Another object of the invention is the use of an open-cell foam on the basis of a cross-linked polyorganosiloxane as a dressing in the negative pressure wound therapy.

Another object of the invention is to provide a ready-to-use set for negative pressure wound therapy, including,
(a) a cover material for air-tight sealing of the wound and the surrounding area,
(b) a means for the generation of a negative pressure in the wound area, preferably a means for the functional connection of the wound area with a negative pressure source outside of the cover material so that a negative pressure can be generated in the wound area, and fluids can be drawn out of the wound area by suction,
c) an open-cell foam on the basis of a cross-linked polyorganosiloxane, whereby the foam is suitable as a dressing and is supplied in a ready-to-use condition.

The new device in accordance with the present invention is distinguished in particular by the fact that it at least includes a wound dressing containing an open-cell foam on the basis of a cross-linked polyorganosiloxane. An advantage of the open-cell foam on the basis of a cross-linked polyorganosiloxane as a constituent of the device in accordance with the present invention consists in the fact that it provides a soft wound dressing for the negative pressure wound therapy.

A further advantage of the open-cell foam on the basis of a cross-linked polyorganosiloxane as a constituent of the device in accordance with the present invention consists in the fact that an adhesion and/or the growing of tissue into the dressing can be largely avoided even over a period of 3 days or more. This avoids traumatization of the wound when the dressing is changed, thereby enhancing the efficacy of the wound therapy.

A further advantage of the open-cell foam on the basis of a cross-linked polyorganosiloxane as a constituent of the device in accordance with the present invention consists in the fact that it allows a negative pressure wound therapy which enables the patient to change the dressing at intervals of 3 days or longer. During the interval of 3 days or longer, the dressing in accordance with the present invention was perceived as pleasant by the patient. Itching and reddening of the skin were generally avoided. When changing the dressing after a period of 3 days or more, there were less unpleasant odors than in the case of conventional dressings. The germ density in the changed dressing was unexpectedly low.

The components (a) to (c) of the device in accordance with the present invention are described in the following.

The device in accordance with the present invention includes a cover material (a) for air-tight sealing of the wound. "Air-tight sealing" does not mean that there is no exchange of gas between the wound area and its surroundings. Rather, "air-tight sealing" in this context means that, taking into account the vacuum pump used, the negative pressure necessary for the negative pressure wound therapy can be maintained. This means that cover materials can also be used which have a slight degree of gas permeability as long as the negative pressure necessary for the negative pressure wound therapy can be maintained.

The air-tight cover material can, for example, be in the form of a solid shell or in the form of a flexible foil. It is also possible to conceive of combinations of fixed frame or dressing plates with flexible foil.

In a preferred embodiment of the invention, the cover material for the air-tight sealing of the wound includes a water-insoluble polymer, or a metal foil. The cover material preferably has a thickness of 10 µm to 10,000 µm, in particular from 25 µm to 100 µm.

In a preferred embodiment of the invention, the cover material (a) is a water-insoluble polymer. Preferably the water-insoluble polymer has a solubility of 10 mg/l or less, more preferably of 1 mg/ml or less, particularly from 0.0001 to 1 mg/ml (determined in accordance with the column elution method pursuant to EU Directive RL67-548-EEC, Annex V, Chapter A6). Examples include polyurethane, polyester, polypropylene, polyethylene, polyamide or polyvinyl chloride, polyorganosiloxane (silicone), or a mixture thereof. The cited polymers are preferably provided in non-cellular form.

It has been demonstrated that the objects explained at the start can be solved in a particularly advantageous manner using a cover material with a specific water vapor permeability. In a preferred embodiment, the cover material has a water vapor permeability of 100 to 2,500 $g/m^2 \times 24$ h, more preferably from 500 to 2000 $g/m^2 \times 24$ h, and even more preferably from 800 to 1,600 $g/m^2 \times 24$ h, in particular from 1,050 to 1,450 $g/m^2 \times 24$ h, determined in accordance with DIN EN 13726-2 at 23° C. and 85% relative humidity. In particular, the combination of a cover film having the aforementioned water vapor permeability with an open-cell foam (c) having the physical properties described below is particularly advantageous.

Finished products which have the aforementioned properties can also be used as cover material. Polyurethane film of the brand Hydrofilm® (Paul Hartmann AG, Germany) or Visulin® (Paul Hartmann AG, Germany) have proved to be especially suitable as cover material for the device in accordance with the present invention.

The cover material is usually fixed around the wound or at the edge of the wound in such a way as to ensure that the wound is sealed air-tight. It can be expedient if the cover material is fully self-adhesive or has a self-adhesive edge. Alternatively, fixing and sealing can be achieved, for example, with an adhesive film, a liquid adhesive or a sealing paste.

In a preferred embodiment of the invention, the cover material is a film of one or more water-insoluble polymers, whereby the foil is either self-adhesive over the whole surface or has a self-adhesive edge.

It is also possible, however, that the cover material is held solely on the wound by the negative pressure generated in the negative pressure wound therapy.

In a preferred embodiment of the invention, the cover material and the means for the functional connection of the wound area with a negative pressure source outside of the cover material are supplied already connected and ready to use. It is most especially preferred that this embodiment contains a film of one or more water-insoluble polymers with a self-adhesive edge, as this arrangement considerably facilitates the application of the dressing.

The device in accordance with the present invention for negative pressure wound therapy includes a means (b) for the generation of a negative pressure in the wound area. In a preferred embodiment, this is a means for the functional connection of the wound area with a negative pressure source outside of the cover material so that a negative pressure can be generated in the wound area and fluids can be sucked out of the wound area.

The expression "negative pressure in the wound area" in the context of the invention describes an air pressure which is lower inside the wound dressing than the atmospheric pressure. "Within the wound dressing" refers to the cavity formed between the cover material and the wound.

The difference between the air pressure inside the wound dressing and the atmospheric pressure is stated in relation to the invention in mm Hg (millimeters of mercury), as this is the convention in the negative pressure wound therapy. 1 mm Hg corresponds to one torr or 133.322 Pa (Pascal). In relation to the invention, the negative pressure, i.e. the difference between the pressure inside the wound dressing and the atmospheric pressure, is stated as a positive numerical value in mm Hg.

In one embodiment of the invention, the negative pressure is a maximum of 500 mm Hg, preferably a maximum of 250 mm Hg. This negative pressure range up to a maximum of 500 mm Hg, preferably a maximum of 250 mm Hg has proved suitable for wound healing. In a preferred embodiment of the invention, the negative pressure is at least 10 mm Hg up to a maximum of 150 mm Hg, more preferably of at least 65 and a maximum of 135 mm Hg.

In general, the negative pressure can be a constant negative pressure (bα) or a time-varied negative pressure (bβ).

In this context "constant negative pressure" (bα) means that the negative pressure is maintained at a largely constant level during the treatment. "Maintained at a largely constant level" means that during the treatment slight changes in the negative pressure, for example by 15% plus or minus, may occur.

A preferred constant negative pressure is the range from at least 80 mm Hg up to a maximum of 150 mm Hg.

In this context "time-varied negative pressure" (bβ) means that the pressure is deliberately varied during the treatment. Deliberate variation of the negative pressure refers to variations of the negative pressure which occur when, after application of the negative pressure dressing, an initial set value for the negative pressure is reached. However, the initial increase phase of the negative pressure, which occurs after application of the dressing up to reaching the initial set value, is not covered by the term "time-varied negative pressure". This applies analogously to the reduction of the negative pressure to the atmospheric pressure necessary at the end of the treatment, which is also not covered by the term "time-varied negative pressure".

The "time-varied negative pressure" is limited downwards by the atmospheric pressure and upwards by a maximum negative pressure of 500 mm Hg, preferably 250 mm Hg, more preferably 150 mm Hg, in particular 125 mm Hg. The actual negative pressure applied during the treatment moves within this range defined by its benchmark values. The "time-varied negative pressure" therefore includes, for example, one or several changes between one or several higher negative pressure values and one or several lower negative pressure values. The term "time-varied negative pressure" also covers one or several deliberate changes during the treatment between the atmospheric pressure and one or several higher negative pressure values.

In a preferred embodiment, the maximum negative pressure for a time-varied negative pressure is 125 mm Hg. In this embodiment, the lower limit for the variation of the negative pressure is the atmospheric pressure. During the treatment the negative pressure varies between or within these benchmark values.

In a further preferred embodiment, the maximum negative pressure for a time-varied negative pressure is 125 mm Hg. The lower limit for the variation of the negative pressure in this embodiment is 20 mm Hg. During the treatment the negative pressure varies between or within these benchmark values.

In both of the aforementioned embodiments, the change between the upper and the lower pressure value can occur periodically or non-periodically. A periodic change is preferred. The time intervals during which the higher negative pressure and the lower negative pressure or atmospheric pressure are maintained can vary in length. Preferably a lower negative pressure is maintained for a longer period than a higher negative pressure. Suitable time intervals in which a certain negative pressure setting or the atmospheric pressure is maintained are for example 1 min, 2 min, 5 min, 10 min, 30 min, 1 h, 12 h or 24 h.

Particularly preferable is a varying negative pressure with the parameters set out below, whereby there is a continuous change in the specified time intervals between the two negative pressure values during the treatment:
a negative pressure of 125 mm Hg for 2 min,
and then
a negative pressure of 20 mm Hg for 5 mm.

The device in accordance with the present invention can also include a means by which the actual negative pressure present in the device can be monitored and adjusted as required. The means can be located in the wound area or at another suitable position. It is possible, for example, to fit a pressure sensor in the negative pressure line between the wound dressing and the negative pressure source.

The device in accordance with the present invention for the negative pressure wound therapy also includes a means for the functional connection of the wound area with a negative pressure source outside of the cover material.

The functional connection can be generated, for example, by a connection line or with a negative pressure connector piece. Negative pressure connector pieces are known in the trade as "ports".

In one embodiment, the means for the functional connection of the wound area with a negative pressure source outside of the cover material consists of at least one connection line. The at least one connection line can be ducted through the cover material.

Alternatively, the at least one connection line can be led under the edge of the cover material.

In both cases the penetration point must be sealed air-tight so that the desired negative pressure can be maintained in the dressing. Sealing can be achieved, for example, with an adhesive foil, an adhesive paste or an adhesive strip.

The connection line can be, for example, a tube, a pipe or any other hollow body. A suitable tube, for example, is a silicone drainage tube.

The connection line preferably has a negative pressure adaptor at the end outside of the wound dressing in order to be connectable to the other components of the negative pressure system.

The connection line has an opening at the end which is inside the wound dressing.

In a further embodiment, the means for the functional connection of the wound area with a negative pressure source outside of the cover material is a negative pressure port which can be fastened to the inside or the outside of the cover material, whereby the cover material has the corresponding openings for this purpose. In this embodiment it is also important to ensure air-tight sealing either of the penetration opening (inside port) or the surface of the dressing (outside port). Sealing can be achieved, for example, with an adhesive foil, an adhesive paste or an adhesive strip. It is also conceivable that the port itself has the corresponding fastening facilities, such as adhesive surfaces.

Suitable negative pressure ports are commercially available. These are typically negative pressure ports which are fastened on the outside of the cover material.

The negative pressure port should also have a negative pressure adapter so that it can be connected to the other components of the negative pressure system.

Alongside the components (a) and (b) described above, the device in accordance with the present invention also has a component (c). The open-cell foam on the basis of a cross-linked polyorganosiloxane (c) used in the device in accordance with the present invention is described in more detail in the following.

Foams are generally materials with cells (open, closed, or both) distributed over their whole mass. Materials thus generally have a raw density (in accordance with DIN 53420) which is lower than the density of the basic substance.

A cell is an individual cavity formed in the manufacture of the foam which is partially or fully enclosed by the cell walls and/or cell struts.

A closed cell is usually a cell which is completely enclosed by its walls and has no connection via the gas phase with the other cells. An open cell is generally a cell which is connected with other cells via the gas phase. In the context of this application, the term open-cell means that in the foam (c) there is at least 60% open cells, preferably at least 90% open cells, even more preferably 98% open cells, in particular essentially 100% open cells with reference to the total number of cells.

The cell wall is generally taken to mean the wall enclosing the cell. The cell wall can also be referred to as the cell membrane. The cell strut is generally taken to mean the area of the cell wall which separates more than two cells. Cell struts are preferably at least 1.5 times the thickness, even more preferably at least twice the thickness of the rest of the cell wall.

A reticulated foam is taken to mean a foam which consists largely of cell struts.

In general, polysiloxanes are synthetic polymers in which silicon atoms are linked by oxygen atoms.

"Cross-linked" generally means that linear polymer chains are cross-linked via covalent bonds (i.e. not at the end of the linear chains). In a preferred embodiment, the cross-linking arises (at least partially) due to the fact that linear polysiloxane chains are linked covalently via carbon atoms. Preferably this cross-linking via carbon atoms can be achieved by the reaction of a polyorganosiloxane containing one or more groups with a $C_2$-$C_6$ alkenyl group with a polyorganosiloxane containing one or more Si—H groups.

In a preferred embodiment, the foam (c) is obtained by reaction of a curable mixture containing the components:
(i) a polyorganosiloxane containing one or more groups with a $C_2$-$C_6$ alkenyl group, preferably containing one or more vinyl groups,
(ii) a polyorganosiloxane containing one or more Si—H groups,
(iii) a foaming agent containing one or more OH groups, and
(iv) an organometallic catalyst.

The components (i) to (iv) of the curable mixture are explained in more detail in the following.

The component (i) can be a polyorganosiloxane which has so-called "M, D, T and Q" units. This is the convention recognized in the state of the art for the designation of structural polysiloxane units in agreement with the number of oxygen atoms bound to silicon. This convention uses the letters M, D, T and Q, in order to use the number of oxygen atoms as abbreviations for "mono", "di", "tri" or "tetra".

In a preferred embodiment, the component (i) of the curable mixture contains a polyorganosiloxane in accordance with the general formula (1):

(1)

in which $R^1$ is independently $C_{1-6}$ alkyl, $C_{1-6}$ haloalkyl, aryl or $C_2$-$C_6$ alkenyl provided that the molecule contains at least one $C_2$-$C_6$ alkenyl group, preferably at least two $C_2$-$C_6$ alkenyl groups or at least three $C_2$-$C_6$ alkenyl groups. The compound in accordance with Formula (1) is thus preferably a linear polyorganosiloxane, which has M and D units.

The $C_2$-$C_6$ alkenyl groups may be, for example, vinyl, allyl and/or hexenyl groups. The $C_2$-$C_6$ alkenyl group is preferably a vinyl group. It is also preferred that the $C_2$-$C_6$ alkenyl group, in particular the vinyl group, is attached at the terminal Si atoms as illustrated in Formula (1a), (1a)

in which $R^1$ is independently $C_{1-6}$ alkyl, $C_{1-6}$ haloalkyl, aryl or $C_2$-$C_6$ alkenyl. In particular, in Formula (1 a) $R^1$=methyl.

In the context of this application, the polyorganosiloxane in accordance with Formula (1) or (1a) is also referred to as component (i-MID) of the curable mixture. In general, "n" is selected in such a way that the viscosity of the polyorganosiloxane lies in the range from 500 to 250,000 mPas, preferably from 600 to 100,000 mPas, more preferably from 1000 to 50,000 mPas, and even more preferably from 1,500 to 20,000 mPas, in particular from 2,000 to 10,000 mPas. In the context of this application the viscosity is always measured at 23° C. and determined in accordance with Ph. Eur. 1997, Method 2.2.10 (Rotation viscosimeter) with the aid of a Brookfield viscosimeter model DV-II (Brookfield Engineering Laboratories Vertriebs GmbH, D-73547 Lorch, Germany).

Alongside the linear component (i-M/D), the component (i) of the curable mixture (i.e. the polyorganosiloxane containing one or more groups with a $C_2$-$C_6$ alkenyl group) can also contain branched polysiloxane components which, alongside M and D units, can also have T and/or Q units. These branched components are referred to as component (i-M/D/T/Q). The explanations above regarding the type and quantity of the $C_2$-$C_6$ alkenyl groups also apply to the component (i-M/D/T/Q). In particular, the component (i-M/D/T/Q) contains at least two $C_2$-$C_6$ alkenyl groups, preferably vinyl groups.

Degree of branching and chain length of the component (i-M/D/T/Q) are generally selected in such a way that the viscosity of the polyorganosiloxane lies in the range from 500 to 250,000 mPas, preferably from 600 to 100,000 mPas, more preferably from 1000 to 50,000 mPas, even more preferably from 1,200 to 20,000 mPas, in particular from 1,500 to 10,000 mPas.

In component (i) of the curable mixture the weight ratio of component (i-MID) to (i-M/D/T/Q) is preferably from 20:1 to 1:10, more preferably from 10:1 to 1:2, even more preferably from 8:1 to 1:1, particularly preferably from 6:1 to 1:1.5, in particular from 5:1 to 1:2.

As component (ii) the curable mixture includes a polyorganosiloxane containing one or more Si—H groups. This polyorganosiloxane preferably contains at least two, in particular at least three Si—H groups per molecule. It is, furthermore, preferable that there is no more than one Si—H bond per Si atom.

In general, in the component (ii), one $C_2$-$C_6$-alkenyl group is bonded to 0.01 to 10%, preferably 0.05 to 5% of the silicon atoms.

In a preferred embodiment, the component (ii) contains a polyorganosiloxane in accordance with the general formula (2), (2)

in which $R^2$ is independently $C_{1-6}$ alkyl, $C_{1-6}$ haloalkyl, aryl or hydrogen. Preferably, this applies provided that one molecule in accordance with Formula (2) contains at least 2, preferably at least 3 hydrogen atoms bound to silicon, whereby the hydrogen atoms are bonded to different silicon atoms. In the above Formula (2) the polyorganosiloxane only has M and D units, which is the preferred case. Alternatively, the polyorganosiloxane may also contain T and/or Q units. In general, 0.01 to 10% of the silicon atoms in the component (ii) have a Si—H bond.

Degree of branching and chain length in the component (ii) are generally selected in such a way that the viscosity of the polyorganosiloxane lies in the range of 500 to 150,000 mPa·s preferably from 600 to 50,000 mPas mPa·s, more preferably from 1000 to 20,000 mPas mPa·s, even more preferably from 1,200 to 15,000 mPas mPa·s, in particular from 1,500 to 10,000 mPa·s.

In a preferred embodiment, the polysiloxane (ii) contains M and D units, whereby only the D units include Si—H bonds. The M units preferably contain methyl residues. The corresponding polyorganosiloxane is illustrated in Formula (2a)

(2a)

in which $R^3$ is an aryl or alkyl residue, in particular methyl, and $R^4$ is an aryl or alkyl residue or hydrogen, in particular methyl or hydrogen.

The reaction of component (i) with component (ii) of the curable mixture results in a cross-linked polyorganosiloxane.

Alongside the components (i) and (ii), the curable mixture also contains a foaming agent (iii), preferably a foaming agent containing one or more OH groups. Examples of compounds which contain one or more OH groups are water (H—OH), polyorganosiloxanes with Si—OH groups and alcohols. $C_1$-$C_{12}$ alcohols are preferably used as a foaming agent (iii). In particular, component (iii) consists of one or more $C_1$-$C_{12}$, alcohols. In general, monoalcohols or di- or polyalcohols are possible. Monoalcohols are preferably used. Examples of suitable alcohols include monoalcohols such as methanol, ethanol, 1-propanol, 2-propanol, 1-butanol, 2-butanol, t-butanol, 1-pentanol, cyclo-pentanol, 1-hexanol, 2-hexanol, cyclo-hexanol, heptanol, octanol or dialcohols such as ethylene glycol, propylene glycol, 1,4-butanediol.

Particular preference is given to monoalcohols with 4 to 6 carbon atoms, in particular 1-butanol, 1-pentanol and 1-hexanol.

To achieve the physical properties described below, it has proved advantageous if the quantity of water in the curable mixture is limited. Preferably the curable mixture should have a water content of 0.0001 to 3 weight percent, more preferably of 0.001 to 2.0 weight percent, and even more preferably of 0.01 weight percent to 1.0 weight percent. The water content is determined here using the coulometric Karl-Fischer method. In general, the water content does not come from the addition of water, but from the residual water content of the components (i) to (iv) of the curable mixture. Reaction of the component (iii) with the component (ii) results in a so-called foaming reaction. This leads to the production of cellular polyorganosiloxanes.

Alongside the components (i) to (iii), the curable composition contains a organometallic catalyst (iv). The organometallic catalyst generally catalyzes the reaction of the component (i) with the component (ii) and the reaction of the component (ii) with the component (iii).

Preferably the organometallic catalyst is an organometallic compound, whereby the metal is selected from group 8 (iron group), group 9 (cobalt group), group 10 (nickel group) or group 11 (copper group). More preferably, the metal is palladium or platinum, particularly platinum.

Numerous types of platinum catalysts are familiar from the state of the art. They include, for example, reaction products of chloroplatinic acid with olefins, alcohols, ethers, aldehydes and vinylsiloxanes such as tetramethyldivinyldisiloxane. A reaction product of chloroplatinic acid with tetramethyldivinyldisiloxane in the presence of potassium bicarbonate, as disclosed in the U.S. Pat. No. 3,775,452, dissolved in xylol up to a quantity of around 5 weight percent of platinum is preferred, and is referred to in the following as the "Karstedt catalyst".

Further examples of suitable platinum catalysts are:

$Pt(CH_3CN)_2Cl_2$,
$\{Pt(CH_2CN)_2(CH_3)_4\}Cl_2$,
$Pt(NH_3)_2Cl_2$,
$K\{PtCl_3CH_2CH_2CH_2OH)\}$,
$PtBr_2(CH_2H_4)_2$,
$K\{PtBr_3(C_2H_4)\}$,
$PtCl_2(C_2H_4)$,
$(CH_3)_2C=CH_2PtCl_2$,
$H_2Pt(CN)_4 \cdot 5H_2O$,
$H\{PtCl_3(CH_2CN)\}$,
$Pt(NH_3)_2(CNS)_2$,
$PtCl_2PCl_3$,
$\{Pt(NH_3)_4\}\{PTCl_4\}$,
$PtCl_2\{P(CH_2CH_3)_3\}_2$,
$PtCl_2\{P(OCH_2CH_3)_3\}_2$,
$Pt(OOCH_2SCH_2CH_3)_2$,
$(CH_3)_4Pt$,
$(CH_3)_3Pt—Pt(CH_3)_3$,
$PtCl_2CO$
and
$PtBr_2CO$.

In the curable mixture, quantities of
100 parts by weight of component (i);
1 to 150 parts by weight, preferably 10 to 80 parts by weight, more preferably 15 to 50 parts by weight of component (ii);
1 to 100, preferably 2 to 50, more preferably 5 to 30 parts by weight of component (iii); and
0.0001 to 10 parts by weight, preferably 0.001 to 5 weight percent, more preferably 0.01 to 3 parts by weight of component (iv) are generally preferred.

The molar ratio of Si—H groups in the component (ii) to the sum of $C_2$-$C_5$ alkenyl groups from the component (i) and OH groups from the component (iii) is generally 5:1 to 1:10, preferably 4:1 to 1:5, more preferably 3:1 to 1:4, even more preferably 2:1 to 1:3, particularly preferred 1.5:1 to 1:2 and in particular 1:0.9 to 1:1.5.

Alongside the components (i) to (iv), the curable mixture can also contain further substances commonly used in the area, such as fillers and additives.

In order to produce an open-cell silicone foam (c), the components described above are mixed in some desired sequence. It is preferred that an initial partial mixture A, containing the components (i), (iii) and (iv), is mixed with a second partial mixture B, containing the components (i), (ii) and (iii). The usual mixing devices can be used, for example a static mixer or a dynamic mixer.

The reaction of the components (i) to (iv) of the curable composition preferably takes place at 20 to 25° C., in particular at 23° C.

The components (i) to (iv) described above are preferably selected in such a way that the result is an open-cell foam on the basis of a cross-linked polysiloxane, in particular a foam with the physical properties described below.

It has been demonstrated that the objects set out above can be solved unexpectedly advantageously if the foam (c) has a specific tensile strength, a specific ductile yield and a specific hardness. In a preferred embodiment, the foam (c) has a tensile strength of 100 kPa to 100 MPa, more preferably 500 kPa to 50 MPa, even more preferably 800 kPa to 10 MPa, measured in accordance with DIN 53571. Furthermore, the foam (c) preferably has a ductile yield of 100% to 350%, more preferably from 160% to 320%, even more preferably from 180% to 300%, measured in accordance with DIN 53571. In addition to this, the foam (c) preferably has a hardness of 20 to 70 Shore A, more preferably from 30 to 60 Shore A, even more preferably from 40 to 50 Shore A, measured in accordance with DIN 53505.

It has also been demonstrated that the objects set out above can be solved unexpectedly advantageously if the foam (c) has a specific air permeability. In a preferred embodiment the foam (c) has an air permeability of 1,000 to 8,000 $l/(m^2 \text{ sec})$, more preferably from 2,000 to 7,500 $l/(m^2 \text{ sec})$, even more preferably from 2,500 to 7,000 $l/(m^2 \text{ sec})$, in particular from 3,000 to 6,500 $l/(m^2 \text{ sec})$, measured in accordance with DIN EN ISO 9237.

It has also been demonstrated that the objects set out above can be solved unexpectedly advantageously if the foam (c) has visco-elastic properties. This means that the behavior of the foam (c) under strain looks like a combination of an elastic solid and a viscous fluid. The visco-elastic behavior can be characterized by a torsional vibration test in accordance with DIN 53445. It is preferred that the foam, when determined in accordance with DIN 53445 at 23° C., has a mechanical loss factor of 0.1 to 1.0, more preferably from 0.15 to 0.8, even more preferably from 0.2 to 0.6.

It has also been demonstrated that the objects set out above can be solved unexpectedly advantageously if the foam (c) has a raw density between 0.12 and 0.35 $g/cm^3$, more preferably between 0.15 and 0.25 $g/cm^3$, in particular between 0.18 and 0.22 $g/cm^3$, measured in accordance with DIN EN ISO 845.

It has also been demonstrated that the objects set out above can be solved unexpectedly advantageously if the foam (c) contains silver in the form of silver ions or in the form of atomic silver. Preferably, a silver coating is applied after production of the foam (c). Alternatively the silver can be added to the curable compound. Preferably the foam (c) contains 0.000001 to 0.1 weight percent, more preferably 0.0001 to 0.01 weight percent of silver in relation to the total weight of the foam (c).

In a preferred embodiment, the open-cell foam is used in a dry condition. Preferably, the foam is not, for example, soaked in an activation solution (e.g. Ringer's solution).

In a preferred embodiment of the invention, the open-cell foam has a thickness of 1 to 50 mm, in particular from 15 to 30 mm.

In a preferred embodiment of the invention, the device for negative pressure wound therapy includes at least a wound contact layer between the foam (c) and the surface of the wound. The additional wound contact layer can be connected to the foam (c) in an adhesive or non-adhesive manner.

In principle, any wound contact layer known from the state of the art can be used as long as the permeation of wound exudate is ensured and the material is not likely to grow into or stick to the wound tissue.

Examples of suitable wound contact layers are described in the German patent applications DE 10 2008 062 472.1, DE 10 2008 031 183.9 and DE 10 2008 031 182.0.

The wound contact layer can also consist of a permeable non-woven layer or a lattice tulle. The permeable non-woven layer or the tulle consists preferably of a hydrophobic material, for example polyester. The tulle may also have a balm and a silver coating. Especially suitable wound contact layers are the medicated dressings of the brand names Hydrotüll® and Atrauman® (Paul Hartmann AG, Germany).

In a further preferred embodiment, the device for negative pressure wound therapy comprises at least one additional pressure distribution layer between the foam (c) and the cover material (a).

The advantage of an additional pressure distribution layer can consist in the fact that the pressure exerted by the dressing on the wound can be more evenly distributed by the use of the pressure distribution layer. Furthermore, the pressure distribution layer can store additional wound exudate.

The additional pressure distribution layer can consist of an open-cell or semi-open-cell foam, a distancing structure, a textile layer, a structured gel or a permeable non-woven layer. Suitable textile layers include, for example, compresses with folded cutting edges or lattice tulles.

The additional pressure distribution layer can be designed in such a way that fluids such as wound exudate can pass through it. For this purpose the pressure distribution layer may have suitable channels or openings, or consist of a material permeable to fluids.

Furthermore, the invention provides a ready-to-use set for negative pressure wound therapy, including the device in accordance with the present invention, whereby the foam (c) is suitable as a wound dressing and is provided in a ready-to-use pack.

The packed foam (c) included in the set can be produced by packing the dry foam (c) in a moisture-proof manner. Preferably, the packed, ready-to-use foam (c) is provided in sterile form. Ideally the foam (c) is provided in a sterile, individually sealed, ready-to-use pack. It can be sterilized using back-pressure vapor sterilization or other suitable sterilization methods with which those skilled in the art would be familiar.

The set can contain further optional components such as, for example, one or more wound contact layers, one or more additional pressure distribution layers, adhesive to fix the dressing, sealing agent to produce an air-tight seal of the dressing, pressure sensors, connection elements for pressure sensors, additional tubes, connection pieces for tubes, disinfectant agent, skincare agents, pharmaceutical preparations or instructions for use. Preferably, the set in accordance with the present invention also contains scissors, dabs and pincers, particularly in sterile form.

The set can include both the at least one wound contact layer and the at least one additional pressure distribution layer.

Preferably the set also contains a ready-to-use negative pressure unit. The negative pressure unit can contain components such as a pump, one or more fluid containers, a control unit, a power supply, electric connection elements and tubes. The negative pressure unit can also contain a device for the functional connection of the negative pressure dressing with an existing stationary negative pressure source. Preferably, all components in which this is necessary for medical reasons are provided in a sterile pack. The advantage of the ready-to-use set consists in the fact that the negative pressure dressing can be applied quickly in a standardized and uncomplicated manner. Another advantage is that all of the components of the set used in the wound area can be provided in a sterilized form.

Another object of the invention is the use of the open-cell foam on the basis of a cross-linked polyorganosiloxane (c) explained above as a dressing in the negative pressure wound therapy. The object of the invention is thus also an open-cell foam on the basis of a cross-linked polyorganosiloxane (c) for use in the negative pressure wound therapy. The object of the invention is thus also the use of an open-cell foam on the basis of a cross-linked polyorganosiloxane (c) in a device for the negative pressure wound therapy, in particular as a wound dressing.

Special advantages of the device in accordance with the present invention, the set in accordance with the present invention or the use or application in accordance with the present invention, arise when the wounds are burn wounds, wounds caused by mechanical trauma, wounds caused by the effects of chemicals, wounds caused by a metabolic disorder, wounds caused by a circulatory disorder or wounds caused by pressure ulcers.

In a further preferred embodiment, an open-cell foam on the basis of a cross-linked polyorganosiloxane (c) is provided for use in negative pressure therapy in the treatment of a wound caused by a skin graft. The application includes the treatment of wounds caused by full-skin and split-skin transplants using negative pressure therapy. Advantageous effects arise due to the soft structure of the open-cell foam (c) and due to the uniform distribution of pressure. When the foam (c) is used in the treatment of a wound caused by a skin graft, the skin graft can be adequately fixed while avoiding undesired shear forces.

The open-cell foam on the basis of a cross-linked polyorganosiloxane (c) described above can be used advantageously as a wound dressing in the negative pressure therapy of pressure wounds in patients with a body-mass index (BMI=body weight over height squared) of less than 18.0, in particular with a body mass index of 14 to 17.5. This applies in particular to patients aged over 60. The advantageous effect of the device in accordance with the present invention or the set in accordance with the present invention is manifested in particular in such patients.

Another object of the invention is a method for the negative pressure wound therapy, including the steps
a) provision of a device or a set as described herein,
b) application of the negative pressure dressing to the wound,
c) production of a negative pressure of a maximum of 500 mm Hg, preferably a maximum of 250 mm Hg in the wound area for at least 30 minutes and up to a maximum of 7 days, preferably for at least 1 day up to a maximum of 6 days.

FIGURES

In the following the device in accordance with the present invention for the negative pressure wound therapy is explained in more detail with the aid of drawings. The inventions, however, should not be seen as being reduced to the embodiments shown in the drawings or in the description of the drawings. Rather, the device in accordance with the present invention can also include combinations of the individual features of the alternative forms.

LEGEND

1 Wound surroundings (i.e. generally undamaged skin)
2 Air-tight cover material (a)
3 Open-cell foam on the basis of a cross-linked polyorganosiloxane (c)
4 Negative pressure connection piece (port)
5 Negative pressure connection line
6 Collector
7 Negative pressure unit
8 Wound
9 Pressure distribution layer
10 Wound contact layer

DESCRIPTION OF THE FIGURES

Figure 1:
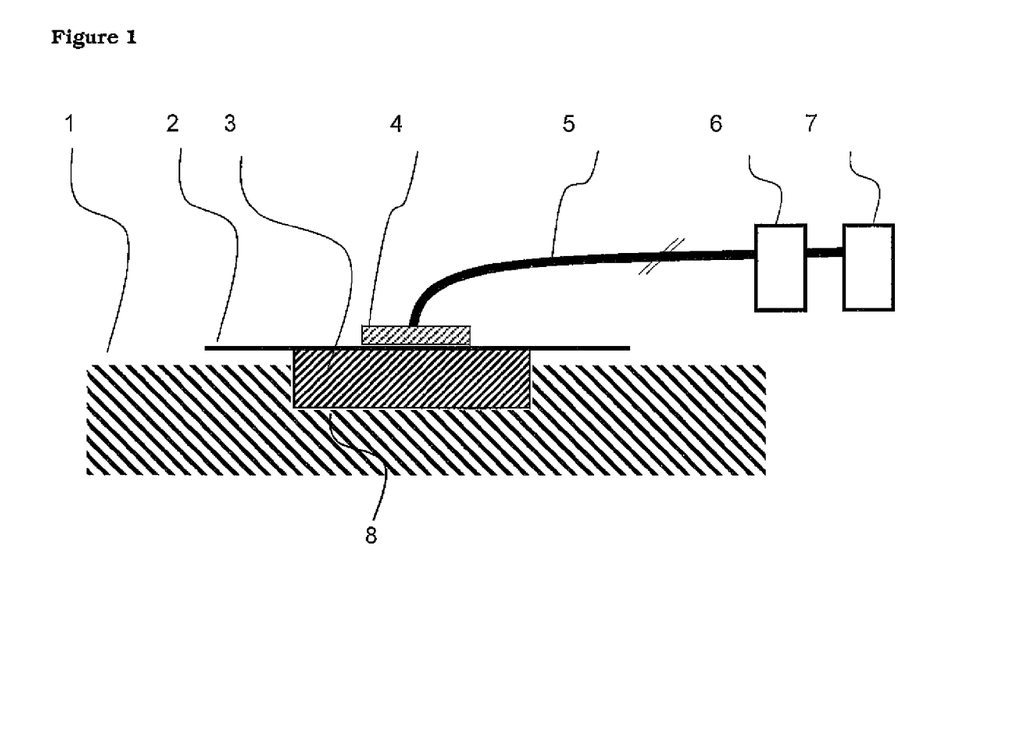
FIG. 1: Diagram of the device in accordance with the present invention (side view)

FIG. 1 shows a side view of the device in accordance with the present invention. The device comprises an air-tight cover material (2), a means (4-5) for the functional connection of the wound area with a negative pressure source (7) located outside of the cover material, and the open-cell polysiloxane foam (3). The cover material (2) is fastened in the area of the wound surroundings (1), generally consisting of undamaged skin. The size of the cover material must be such that the cover material can be fastened outside of the wound area in the area of the wound surroundings (1). The cover material (2) can have different dimensions and shapes, for example circular, oval or rectangular. It can also have an irregular shape matched to the individual wound. The cover material (2) can be a non-transparent material, a partially transparent material or a fully transparent material. The cover material (2) is generally fastened in the area of the wound surroundings (1) and sealed air-tight. This can be achieved, for example, by providing an adhesive edge on the cover material (2). As far as possible, the adhesive edge should be protected until the dressing is applied by protective strips. Alternatively an adhesive substance can be applied either to the edge of the cover material (2) and/or the intact skin around the wound. This has the advantage that it is easier to match the cover material to the shape and size of the wound. The fastening and air-tight sealing of the device can, however, also be achieved by the use of adhesive strips or an adhesive paste. In the preferred embodiment shown here, the port (4) is attached to the outside of the air-tight cover material (2). In order to functionally connect the wound area with a negative pressure unit (7) located outside of the cover material in this arrangement, there must be one or more openings passing through the cover material (2) in the proximity of the port (4). In addition to this, an air-tight seal has to be ensured. Such a seal can be achieved, for example if a foil (not shown in FIG. 1) is applied on the upper side of the port pointing away from the wound which is adhered to the cover material (2). The application of the dressing is made easier if a port is used which already has a suitable means of fastening and sealing to fasten the port to the cover material. This is the case for example in the commercially available PPM-Drainageport® by the company Phametra-Pharma and Medica-Trading GmbH (Herne/Ruhrstadt, Germany).

FIG. 1 also shows an open-cell polysiloxane foam (3). When the dressing is applied, this should be placed in the wound area in such a way that cavities are kept to a minimum and good contact with the wound (8) is ensured.

Figure 2:
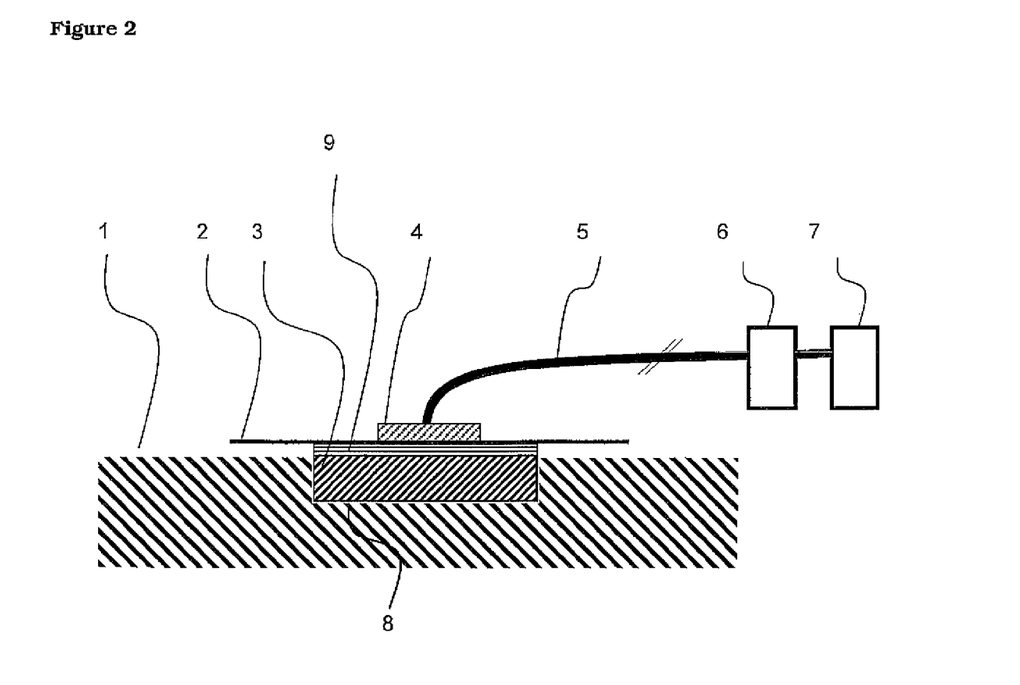
FIG. 2: Diagram of a further embodiment with wound contact layer

An example of the use of a wound contact layer (10) in the device in accordance with the present invention is shown in a side view in FIG. 2. This is a preferred embodiment of the device in accordance with the present invention. The wound contact layer (10) should be such that the wound exudate can pass through the wound contact layer (10). It is also possible to use several wound contact layers and to combine different types of wound contact layer.

Figure 3:
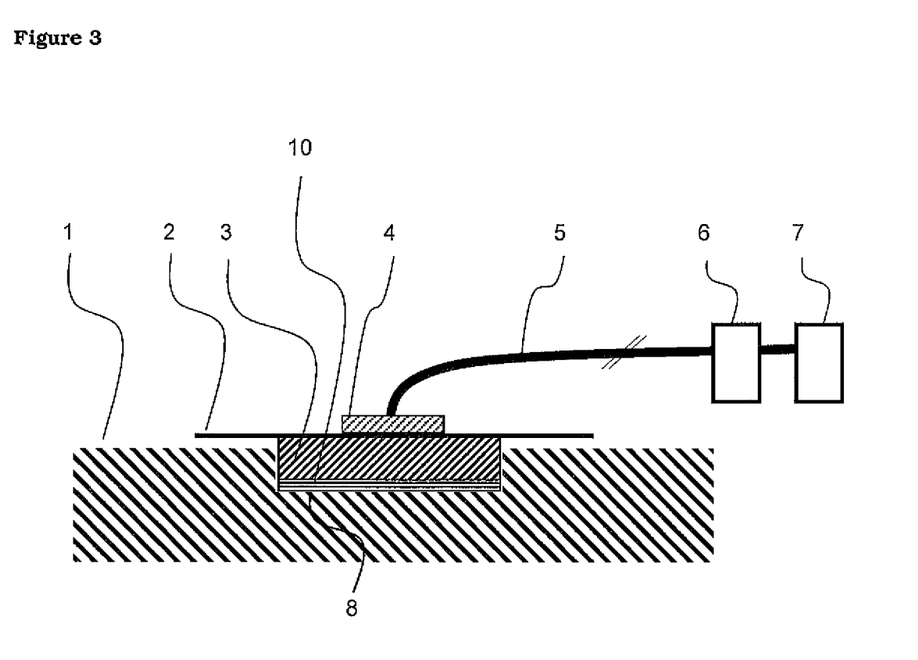
FIG. 3: Diagram of a further embodiment with pressure distribution layer

FIG. 3 shows a diagram of a side view of another preferred embodiment of the device in accordance with the present invention. This embodiment is distinguished by the presence of an additional pressure distribution layer (9). It is also possible to use several pressure distribution layers, whereby different pressure distribution layers can be combined. It must also be pointed out that a combination of the wound contact layer with the additional pressure distribution layer shown in FIG. 2 is also covered by the invention and represents an especially preferred embodiment.

The pressure distribution layer (9) can be designed in such a way that fluid such as wound exudate can pass through it. For this purpose the pressure distribution layer can have suitable channels or openings. Alternatively it can consist of a material, which allows the passage of wound exudates without any further measures.

The additional pressure distribution layer (9) can be designed in such a way that it is coordinated with the means for the functional connection of the wound area with a negative pressure source outside of the cover material. Such coordination could consist for example, in the pressure distribution layer(s) having a cavity to accommodate the end of the tube or the port. Other adaptations are possible.

The pressure distribution layer can be connected with the open-cell foam (c) in an adhesive or non-adhesive manner.

The invention is illustrated by the following example.

EXAMPLE

Production of the Open-Cell Foam (c)

Partial Mixture A:
60 parts vinyl group-containing M/D polysiloxane with a viscosity of 6,000 mPas (i)
30 parts vinyl group-containing M/D/Q polysiloxane with a viscosity of 5,500 mPas (i)
3 parts n-butanol (iii)
0.1 part Pd catalyst (Karstedt)
Partial Mixture B:
30 parts vinyl group-containing M/D polysiloxane with a viscosity of 6,000 mPas (i)
10 parts vinyl group-containing M/D/Q polysiloxane with a viscosity of 5,500 mPas (i)
30 parts Si—H group-containing M/D polysiloxane with a viscosity of 4,500 mPas (iii)

Partial mixtures A and B were mixed in a static mixer at 22° C. and caused to react with each other. After 20 minutes the resulting foam could be removed and cut to the desired size.

The resulting foam was characterized by the following parameters:
Density: 0.22 g/cm³, tensile strength>150 KPa, ductile yield>200%, air permeability 4,000 l/(m² sec)

The invention claimed is:
1. A device for negative pressure wound therapy comprising,
    (a) a cover material for air-tight sealing of the wound and the wound surroundings;
    (b) a means suitable for the generation of a negative pressure in the wound area; and
    (c) an open-cell foam on the basis of a cross-linked polyorganosiloxane as a wound dressing,
    wherein the foam (c) has an air permeability of 1,000 to 8,000 l/(m² sec), measured in accordance with DIN EN ISO 9237, and
    whereby the foam (c) is obtained by the reaction of a curable mixture containing the components
    (i) a first polyorganosiloxane containing one or more groups with a $C_2$-$C_6$ alkenyl group,
    (ii) a second polyorganosiloxane containing one or more Si—H groups,
    (iii) a foaming agent containing one or more OH groups, and
    (iv) an organometallic catalyst.
2. The device for negative pressure wound therapy in accordance with claim 1, wherein the cross-linked polyorganosiloxane consists of (i) the first polyorganosiloxane containing one or more groups with a $C_2$-$C_6$ alkenyl group, cross-linked to (ii) the second polyorganosiloxane containing one or more Si—H groups.
3. The device for negative pressure wound therapy in accordance with claim 1, whereby the component (i) contains a polyorganosiloxane in accordance with general formula (1),

(1)

in which $R^1$ is independently $C_{1-6}$ alkyl, $C_{1-6}$ haloalkyl, aryl or $C_2$-$C_6$ alkenyl, provided that n has a value such that the viscosity of the polyorganosiloxane is in a range between 500 and 250,000 mPa·s and that the molecule contains at least one $C_2$-$C_6$ alkenyl group.
4. The device for negative pressure wound therapy of claim 1, whereby the component (ii) contains a polyorganosiloxane in accordance with general formula (2), (2)

in which $R^2$ is independently $C_{1-6}$ alkyl, $C_{1-6}$ haloalkyl, aryl or hydrogen, provided that the molecule contains at least two hydrogen atoms bonded with silicon, whereby they are bonded to different silicon atoms, and n has a value such that the viscosity of the polyorganosiloxane of component (ii) is from 500 and 150,000 mPa·s.
5. The device for negative pressure wound therapy of claim 2, whereby a $C_1$-$C_6$ alcanol is used as component (iii).
6. The device for negative pressure wound therapy of claim 1, whereby the foam has a tensile strength of 100 kPa to 10 MPa, measured in accordance with DIN 53571 and/or a ductile yield of 100% to 350%, each measured in accordance with DIN 53571.
7. The device for negative pressure wound of claim 1, wherein the polyorganosiloxane (i) contains one or more vinyl groups.
8. The device for negative pressure wound therapy of claim 1, whereby the foam (c) has visco-elastic properties.
9. The device for negative pressure wound therapy of claim 1, whereby the foam (c) has a raw density between 0.12 and 0.30 g/cm³, measured in accordance with DIN EN ISO 845.
10. The device for negative pressure wound therapy of claim 1, whereby the cover material (a) has a water vapor permeability of 100 to 2,500 g/m²×24 h.
11. The device for negative pressure wound therapy of claim 1, also containing at least one additional pressure distribution layer for insertion between the wound dressing (c) and the cover material (a).
12. The device for negative pressure wound therapy of claim 1, also containing a wound contact layer for insertion between the surface of the wound and the wound dressing (c).
13. A ready-to-use set for negative pressure wound therapy comprising,
    a) a cover material for air-tight sealing of the wound and the wound surroundings,
    b) a functional connection of the wound area with a negative pressure source outside of the cover material in such a way that a negative pressure can be generated in the wound area and fluids can be drawn out of the wound area by suction,
    c) an open-cell foam on the basis of a cross-linked polyorganosiloxane containing (i) a first polyorganosiloxane, said first polyorganosilaxane containing one or more groups with a $C_2$-$C_6$ alkenyl group, covalently linked via carbon atoms to (ii) a second polyorganosiloxane, said second polyorganosiloxane containing one or more Si—H groups, whereby the foam is suitable as a wound dressing and is provided in a ready-to-use pack.
14. A method for negative pressure wound therapy, said method comprising
    providing the device of claim 1,
    dressing a wound with the open-cell foam on the basis of a cross-linked polyorganosiloxane and applying a negative pressure in the wound area.
15. The method of claim 14 for the treatment of pressure wounds in patients with a body mass index of less than 18.
16. The method for negative pressure wound therapy of claim 14, whereby the component (i) contains a polyorganosiloxane in accordance with general formula (1), (1)

in which $R^1$ is independently $C_{1-6}$ alkyl, $C_{1-6}$ haloalkyl, aryl or $C_2$-$C_6$ alkenyl, provided that n has a value such that the viscosity of the polyorganosiloxane is in a range between 500 and 250,000 mPa·s and that the molecule contains at least one $C_2$-$C_6$ alkenyl group.

17. The method for negative pressure wound therapy of claim 14, whereby the component (ii) contains a polyorganosiloxane in accordance with general formula (2),

(2)

in which $R^2$ is independently $C_{1-6}$ alkyl, $C_{1-6}$ haloalkyl, aryl or hydrogen, provided that the molecule contains at least two hydrogen atoms bonded with silicon, whereby they are bonded to different silicon atoms, and n has a value such that the viscosity of the polyorganosiloxane of component (ii) is from 500 and 150,000 mPa·s.

18. The method for negative pressure wound therapy of claim 14, whereby a $C_1$-$C_6$ alcohol is used as component (iii).

19. The method for negative pressure wound therapy of claim 14, said method further comprising air-tight sealing of the wound and the wound surroundings with a cover material.

20. The device for negative pressure wound therapy in accordance with claim 2, wherein the first polyorganosiloxane is of formula (1), (1)

in which $R^1$ is independently $C_{1-6}$ alkyl, $C_{1-6}$ haloalkyl, aryl or $C_2$-$C_6$ alkenyl, provided that n has a value such that the viscosity of the first polyorganosiloxane is in a range between 500 and 250,000 mPa·s and that the molecule contains at least one $C_2$-$C_6$ alkenyl group, the second polyorganosiloxane is of formula (2), (2)

in which $R^2$ is independently $C_{1-6}$ alkyl, $C_{1-6\ 6}$ haloalkyl, aryl or hydrogen, provided that the molecule contains at least two hydrogen atoms bonded with silicon, whereby they are bonded to different silicon atoms, and n' has a value such that the viscosity of the second polyorganosiloxane lies in the range of from 500 to 150,000 mPa·s, and wherein the first polyorganosiloxane and the second polyorganosiloxane are cross-linked covalently via at least one carbon atom, achieved by reaction of the at least one $C_2$-$C_6$ alkenyl group of the first polyorganosiloxane with at least one of the Si—H groups of the second polyorganosiloxane.

* * * * *